United States Patent [19]

Mack

[11] Patent Number: 4,803,050
[45] Date of Patent: Feb. 7, 1989

[54] METHOD AND APPARATUS FOR LIQUID ADDITION AND ASPIRATION IN AUTOMATED IMMUNOASSAY TECHNIQUES

[75] Inventor: Daniel R. Mack, Half Moon Bay, Calif.

[73] Assignee: Sequoia-Turner Corporation, Mountain View, Calif.

[21] Appl. No.: 888,848

[22] Filed: Jul. 22, 1986

Related U.S. Application Data

[63] Continuation-in-part of Ser. No. 757,525, Jul. 22, 1985, abandoned.

[51] Int. Cl.⁴ ............................................. G01N 35/06
[52] U.S. Cl. ........................................ 422/65; 422/67; 422/100; 436/47; 73/864.24
[58] Field of Search ...................... 23/864.24; 141/270, 141/283; 422/63–65, 67, 100; 436/47, 49

[56] References Cited

U.S. PATENT DOCUMENTS

| | | |
|---|---|---|
| 775,307 | 11/1904 | Ortmann et al. . |
| 3,143,393 | 8/1964 | De Seguin Des Hons ...... 422/67 X |
| 3,684,452 | 8/1972 | Bessman ............................ 422/64 |
| 3,708,264 | 1/1973 | Jottier . |
| 3,836,329 | 9/1974 | Jordan . |
| 3,879,987 | 4/1975 | Yasuhiro et al. . |
| 3,951,605 | 4/1976 | Natelson . |
| 4,053,284 | 10/1977 | Posch . |
| 4,058,370 | 11/1977 | Suovaniemi . |
| 4,271,123 | 6/1981 | Curry et al. . |
| 4,298,570 | 11/1981 | Lillig et al. . |
| 4,363,782 | 12/1982 | Yamashita . |
| 4,366,119 | 12/1982 | Takeuchi . |
| 4,399,711 | 8/1983 | Klein . |
| 4,413,534 | 11/1983 | Tomoff et al. .................... 422/65 X |
| 4,495,149 | 1/1985 | Iwata et al. . |
| 4,517,160 | 5/1985 | Galle et al. . |
| 4,522,921 | 6/1985 | Ogawa ............................. 436/45 X |
| 4,528,158 | 7/1985 | Gilles et al. . |
| 4,539,855 | 9/1985 | Jacobs . |
| 4,554,839 | 11/1985 | Hewett et al. . |
| 4,629,703 | 12/1986 | Uffenheimer ..................... 436/45 |

FOREIGN PATENT DOCUMENTS

| | | |
|---|---|---|
| 475326 | 8/1976 | Australia . |
| 69986 | 7/1981 | European Pat. Off. . |
| 55-162062 | 12/1980 | Japan . |
| 56-2560 | 1/1981 | Japan . |
| 57-50659 | 3/1982 | Japan . |

OTHER PUBLICATIONS

"Tandem-E HCG ImmunoEnzyMetric Assay for the Qualitative and Quantitative Measurement of Human Chorionic Gonadotropin (HCG) in Serum", Hybritech, Inc., San Diego, Calif., Aug. 1983.

*Primary Examiner*—Benoit Castel
*Assistant Examiner*—Richard D. Jordan
*Attorney, Agent, or Firm*—Limbach, Limbach & Sutton

[57] ABSTRACT

Apparatus and method for adding liquid to, aspirating liquid from, a rack of reaction tubes wherein a rack and carriage-dependent probes are made to move relative each other in the horizontal and vertical planes. The method calls for performing the first half of a wash sequence on tube located at x row, y column, then completing the sequence on tube at $(x-1)$ row, y column, and returning to the tube at x row, $(y+1)$ column to initiate the first half of the sequence. This "backtracking" of probes permits an incubation-soak period without cumulatively extending the total rack processing time.

6 Claims, 6 Drawing Sheets

METHOD AND APPARATUS FOR LIQUID ADDITION AND ASPIRATION IN AUTOMATED IMMUNOASSAY TECHNIQUES

This application is a continuation in part of copending application Ser. No. 757,525 filed on July 22, 1985, now abandoned, and assigned to a common assignee as the present application.

TECHNICAL FIELD

This invention relates generally to liquid addition and aspiration in immunoassay techniques, and more specifically to methods and apparatus which enable the performance of the necessary washing cycles in a relatively short period of time while meeting the assay specifications for removal of unbound components.

BACKGROUND OF THE INVENTION

Several common immunoassay techniques utilize solid support-antibody complexes to accomplish the detection of specific antigens or antibodies in the sample serum. See, e.g., the immunoassay methods described in U.S. Pat. No. 4,376,110, the relevant portions of which are hereby incorporated by reference into the present application. Typically, the solid support is a plastic bead. After the sample serum and antibody-solid support complex have been incubated for a period of time in the presence of a conjugate, a wash step is required to remove unbound chemical species from the solid support prior to the introduction of reagents; which are used in subsequent reactions which reactions result in the formation of a measurable characteristic, e.g., fluorescence. Immunoassay techniques, however, are extremely sensitive. The presence of trace amounts of unbound components can dramatically affect the subsequent reactions and thereby alter the assay results. When the immunoassay technique is performed manually, the bead can be soaked for a period of time to remove all traces of unreacted materials. The washing step can also be repeated several times to accomplish the desired result. A more completed description of the requirements and suggested techniques for this wash step can be found in the product literature which accompanies Tandem-E Immunoassay Kits marketed by Hybritech, Inc., San Diego, Ca. The relevant portions of that product literature are hereby incorporated by reference into this application.

In the automation of immunoassay techniques, an extended soaking period is not possible if the instrument is to be capable of completing one rack of reaction tubes before the end of an incubation period for a second rack of tubes. Without soaking, however, the twenty-five parts per million specification of the assay protocol is difficult to meet.

The instant invention makes possible the automation of the wash step providing methods and apparatus which are capable of removing unbound components and serum from reaction tubes in a suitably short period of time while simultaneously accomplishing the twenty-five parts per million specification.

It is therefore an object of this invention to provide apparatus and methods which make possible the automation of the routine operation of removing unreacted components from the solid support and reaction tube used in immunoassay techniques.

It is a further object of this invention to provide a simple system for performing the wash step on a rack of reaction tubes in a short cycle time, thereby enabling sufficient through-put to meet the demands of clinical use.

It is another object of this invention to remove unreacted components from the solid support and tubes with detergent solutions without having to remove the rack of tubes from the instrument to soak.

These, and other objects of this invention, shall become apparent to those skilled in the art with reference to this specification and the accompanying figures to which it refers.

SUMMARY OF THE INVENTION

The present invention provides an apparatus and method for adding liquid to, and aspirating liquids from, tubes which comprises means for receiving and positioning a rack of reaction tubes, said rack having n rows in the x-direction and m columns in the y-direction arranged in a rectangular matrix; a carriage; at least one liquid probe depended from said carriage and selectively moveable along said probe longitudinal axis relative to said carriage; means for selectively moving said carriage in the x-direction or y-direction; means for selectively registering the liquid probe with a row of tubes in said rack; control means for actuating said rack positioning means to move said rack discrete distances in the y-direction, substantially equivalent to one column of tubes, relative to said probe, and for selecting movement of said carriage in the x-direction or y-direction; wherein said control means, for each of $y=1$ to m columns is set to first deliver liquid from the probe to a tube located in x row, y column, then to aspirate through the probe previously-added liquid in a tube located at $(x-1)$ row, y column, and then to return said carriage, rack and probe to register said probe with the tube in x row, $(y+1)$ column, wherein $x=1$ to n rows.

DETAILED DESCRIPTION OF THE INVENTION

The methods and apparatus which are the subject of this invention are only part of the overall instrument which permits automated performance of immunoassay techniques. Other features of the preferred embodiment of this invention are described and claimed in several copending applications, including my applications for METHOD AND APPARATUS FOR AUTOMATED, MULTI-SEQUENTIAL IMMUNOAS- SAYS (Ser. No. 757,676), and for METHOD AND APPARATUS FOR DILUTION AND MEASUREMENT (Ser. No. 757,785), as well as applications assigned to a common assignee entitled TUBE TRAP APPARATUS (Ser. No. 757,646), PROBE WASH STATION (Ser. No. 757,742), and IMPROVED TUBE TRAP APPARATUS (Ser. No. 850,941). The relevant portions of all of these applications are hereby incorporated by reference into this application.

The preferred embodiment of this invention comprises the reaction processor module of the Hybritech Immunochemistry Analyzer. Typically, "sandwich" type immunoassays will be performed on this instrument, but the performance of other immunoassay techniques are intended to be within the scope of this invention.

GENERALIZED IMMUNOSSAY TECHNIQUE

According to the protocol developed for the Immunochemistry Analyzer, the instrument transfers sample fluids from a tray of sample cups to reaction tubes which are held in a rectangular rack. Each reaction tube contains a specific monoclonal antibody which has been bound, in this preferred embodiment, to a solid bead. A more complete description of sandwich immunoassay techniques is found, e.g., in U.S. Pat. No. 4,376,110, relevant portions of which are hereby incorporated by reference. First, the sample serum is introduced to the reaction tube. Then, a reagent is added to the reaction tube. The resulting rack of tubes is then removed from the sample processor module of the Immunochemistry Analyzer to incubate (antigenantibody reaction) for some period of time. In the sandwich immunoassay technique, this first step of processing and incubating results in the formation of an antigen "sandwich." The antigen to be detected and determined by the immunoassay is separated from the solution and immobilized by becoming bound between the solid-supported antibody and the reagent which is typically a second antibody which also immunochemically binds to the antigen to be detected.

When the rack of reaction tubes is returned to the Immunochemistry Analyzer after a suitable antibodyantigen incubation time related to the particular immunoassay to be performed, and is loaded into the reaction processor module, all traces (usually 25 ppm specified) of unreacted components in the reaction tubes must be removed from the solid support. This wash step is followed by the addition of a second reagent, in this preferred embodiment a substrate, which will react in the presence of the solid-bound enzyme "sandwich" to form a chromophore. This chromophore then can be spectrophotometrically-analyzed to determine the presence of, and the concentration of, the target antigen in the sample serum. The formation of, and quantitative measurement of concentration of, this chromophore (or other equivalently "labeled" compound) is particularly sensitive to the presence of unreacted components. Since the concentration of antigen to be determined is usually $<10^{-4}$M, common assay specifications require that unreacted components be present at levels below twenty-five parts per million prior to the addition of substrate. It will be recognized by those skilled in the art that although this embodiment utilizes spectrophotometry other signal-producing reactions may be used in the immunoassay technique, e.g. fluorescence and radioisotopes. Each technique, however, has similar specifications for the removal unreacted species, independent of the signal detected.

Another important factor in the automation of immunoassays involves time. To be able to use an automatic instrument in a clinical environment, the instrument must be capable of nearly simultaneous, or sequential performance of the same, or different, immunoassay techniques. Since the length of the incubation period is an important parameter in the technique, and since its length must be reliably reproducible, the automatic immunoassay instrument should be able to accomplish the unbound component washing step quickly to permit other racks of tubes to be similarly washed within the constraints of the overall cycle time limitations. Thus, it is desirable to provide a wash and substrate addition cycle whose cycle length is comparable to the antibody-antigen incubation period. This matched cycling increases the attractiveness of the automated procedure in a clinical environment. This invention recognizes that reproducible and efficient cycle times can be achieved by providing multiple liquid probes which are offset from each other by columns and by permitting rapid position change from row to row. To optimally achieve the necessary cycle time without introducing unacceptable delay, the present invention focusses cycle times upon each individual tube, rather than a row, column or rack of tubes. In this way, efficiency and reproducibility are both addressed.

When the unbound component wash step of the immunoassay protocol is practiced manually upon a small number of tubes, the wash step usually involves a soaking period to dislocate unreacted components which have been absorbed on the solid surface. This soaking period, however, could not be easily accommodated in an automated process as a result of the time constraints described above. However, we found, that without allowing for some soaking, the twenty-five parts per million specification for unbound components proved difficult to satisfy on a consistent basis.

By way of this background, the importance of the method and apparatus of the instant invention can be more fully described with reference to a particularly preferred embodiment.

Reaction Processor Module

Figure 1:
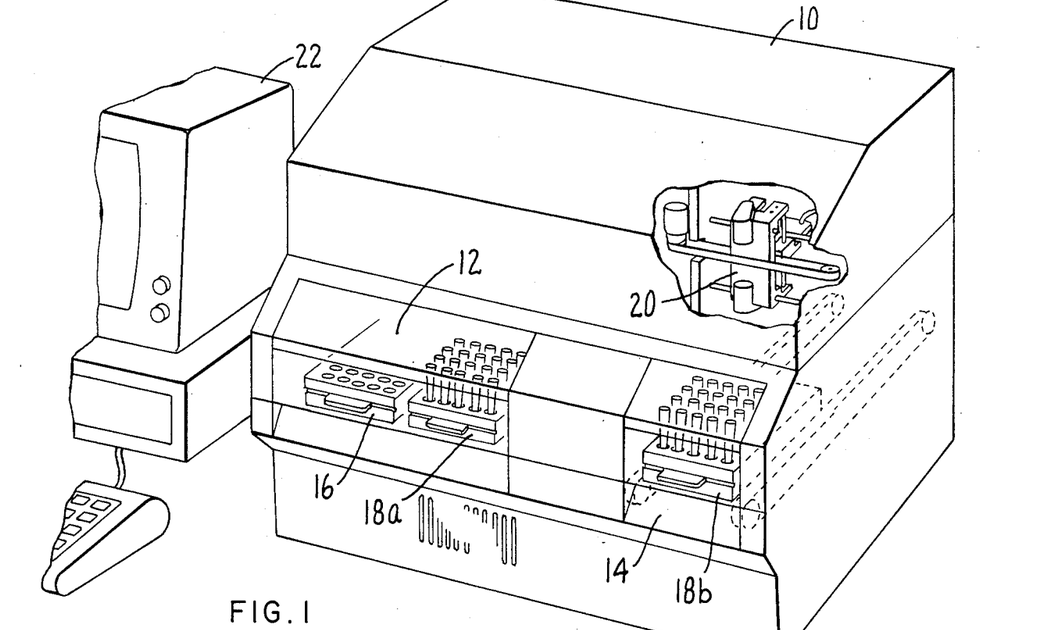
FIG. 1 is a plan view of an instrument embodying the apparatus of the present invention.

The Immunochemistry Analyzer 10 is shown in FIG. 1. The analyzer has a sample processing module 12 and a reaction processor module 14. Sample cups held in rack 16 are loaded into the sample module 12 where the serum is transferred from cups in rack 16 to reaction tubes held in rack 18a. In the preferred embodiment, each of the reaction tubes contains a solid sphere to which is bound one member of the immunological pair used in the "sandwich" technique. After the diluted serum is placed in the reaction tubes and conjugate reagent has been added, the entire rack 18a is removed from the instrument and undergoes a carefully timed antibody-antigen incubation period, the length of which is determined by the particular assay protocol.

At the end of the antibody-antigen incubation period, the operator returns the rack 18b containing reaction tubes to the reaction processor module 14. As seen through the partially broken away front face of the unit 10, carriage 20 is positioned above the rack 18b to effect horizontal (x-direction) and vertical (z-direction) movement of the probes relative to the rack 18b and tubes therein. In this preferred embodiment, a personal computer 22, e.g. an IBM PC-XT, is programmed to control the movement of the carriage 20 and to time the various steps of the assay protocol, both on and off of the instrument 10.

Figure 2:
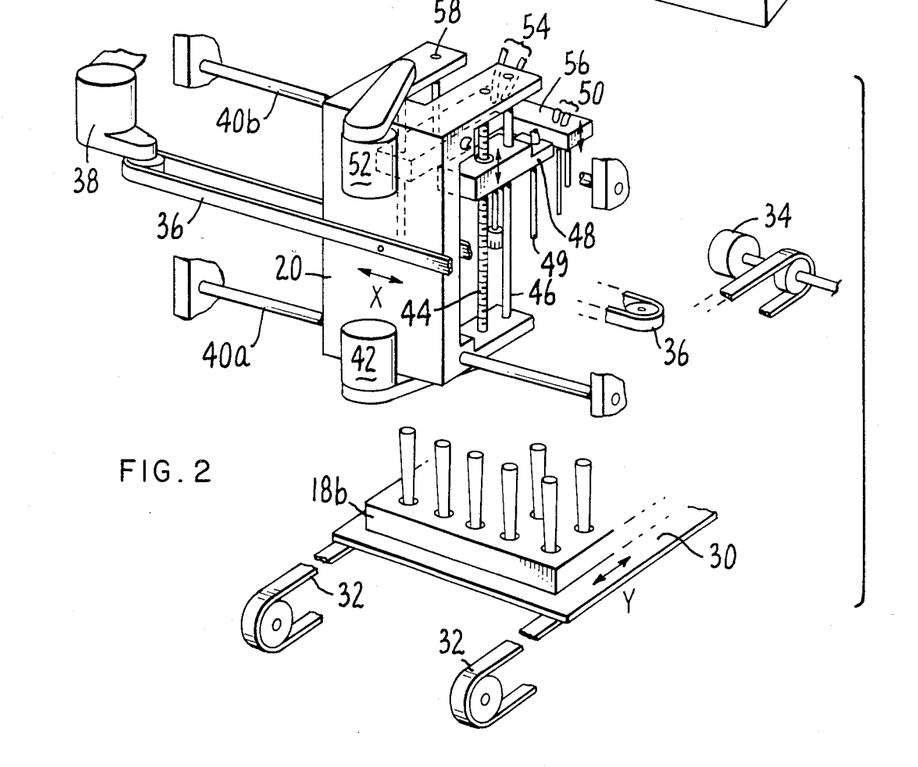
FIG. 2 is an exploded view of the reaction processor module, including the carriage, rack and related drives.

The reaction processor module of the preferred embodiment is shown in greater detail in FIG. 2. The reaction tube rack 18b consists of a rectangular array of rows (in the x-direction) and columns (in the y-direction) of apertures for receiving reaction tubes. In the preferred embodiment, carriage 20 moves across the rows and has no component of movement in the "column" vector. However, those skilled in the art will appreciate that an apparatus which has a y-direction carriage is intended to be within the scope of this invention. In this preferred embodiment, movement of the rack 18b in the y-direction, relative to the carriage 20, is accomplished by a table 30 underneath the rack 18b. The table 30 is motor-driven with a single axis of movement in the "column" or y-direction. The y-direction movement of this platform is controlled by table drive belts 32, table motor 34 and an automatic controller which in this preferred embodiment comprises an IBM personal computer. The controller can control the table 30 movement in discrete units equivalent to the width of one row relative to the carriage. The controller also controls the movement of the carriage 20 in discrete movements equivalent to the width of one column. Thus, the controlled movement of the carriage 20 and the table 30, permits the probe assembies which are attached to the carriage 20, to register the liquid probes with every tube contained within the rectangular matrix.

The carriage 20 is conveyed in the x-direction by carriage drive belt 36, driven by a carriage motor 38. Guide rods 40a and 40b insure accurate movement of the carriage in the x-direction to permit proper registration of the probes with the tube mouths.

Vertical movement of the first probe is accomplished by a first probe motor 42 which drives jack screw 44. A guide rod 46 fixes the position of a first probe assembly 48 in the horizontal plane, to permit registration of the optics-aspirate probe 49 with the reaction tubes. In one of the final steps of the immunoassay protocol probe 49 aspirates quenched, substrate fluid from the tubes into an optics module for quantitative, optical determination of analyte concentration. Second probe motor 52 controls vertical movement of probes 50 and 54 which are depended from a second probe assembly 56. The probe motor 52 drives a jack screw (shown in dashed lines) fixed to the bottom of the carriage 20. Guide 58 fixes the horizontal position of the probe assembler 56. The direction of the jack screw drives determines whether the probe assemblies ascend or descend. Probes 50 add substrate reagent and quench reagent. Probes 54 add detergent solution to, and aspirate the same from, the tubes.

Figure 3:
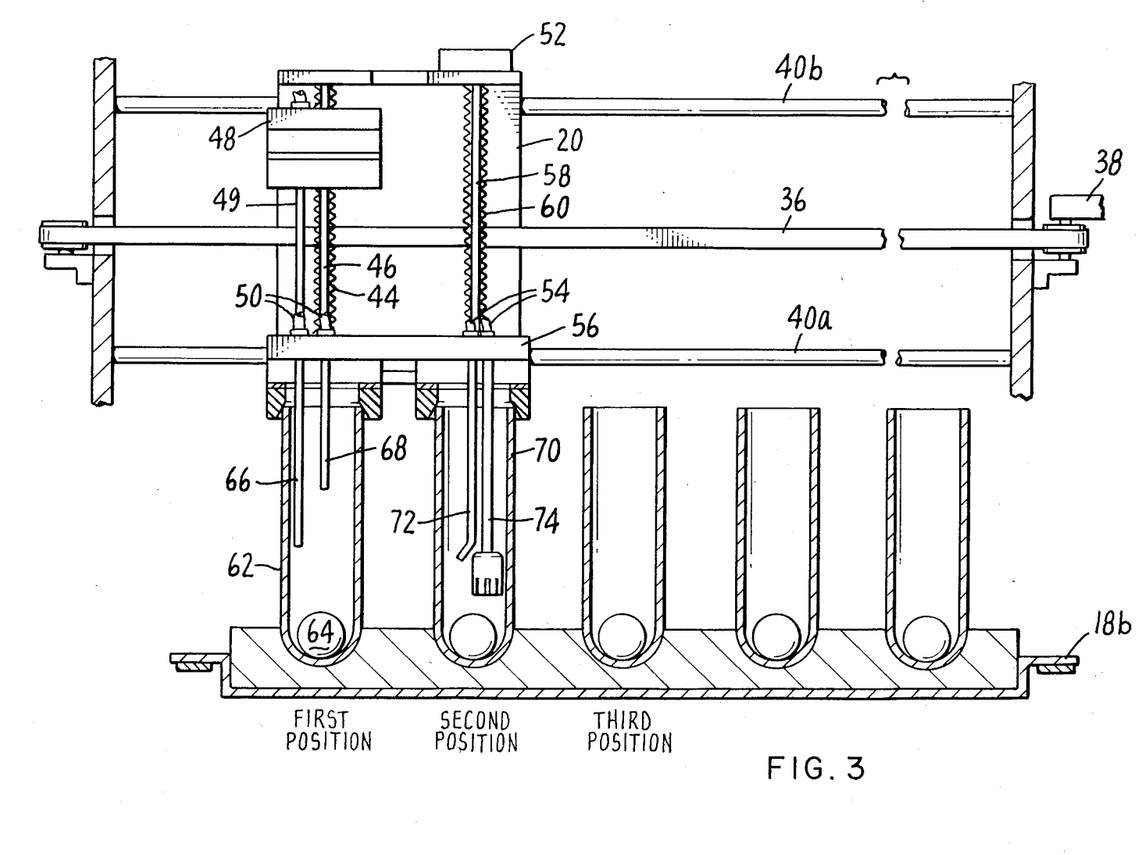
FIG. 3 is a perspective view taken along the lines A—A, of FIG. 2 showing the detergent-dispensing, wash-aspirate, diluent/quench, substrate and optics-aspirator probes of the reaction processor module.

Referring now to FIG. 3, second probe assembly 56 and its associated mechanisms can be seen here clearly. Guide 58 and jack screw 60 are shown in relation to be second probe motor 52 which drives jack screw 60.

FIG. 3 shows a reaction tube 62 into which a spherical support 64 is placed according to the immunoassay protocol. Typically, the surface of the solid support will have bound to it one member of the immunological antigen-antibody pair, dependent upon the assay protocol being practiced. Depending from the first probe assembly 48 is the optics-aspirate probe 49, shown in the retracted position. This probe is offset by one row from the probes 66 and 68, but in the same column. Substrate dispensing probe 66 and quench/diluent dispensing probe 68 occupy one tube position on first probe assembly 56. In a tube 70, identified as being in the "second" position in rack 18b, detergent dispensing probe 72 and aspirating probe 74 are depended from the second probe assembly 56 at a second position, in the same row as the probes 66 and 68, but in a different column. It is also shown in FIG. 3 that the probes and their respective assemblies can be withdrawn from the tubes to permit movement of either the carriage 20 or the rack 18b, or both, without damage to the probes, their supporting assemblies or the tubes.

Figure 4:
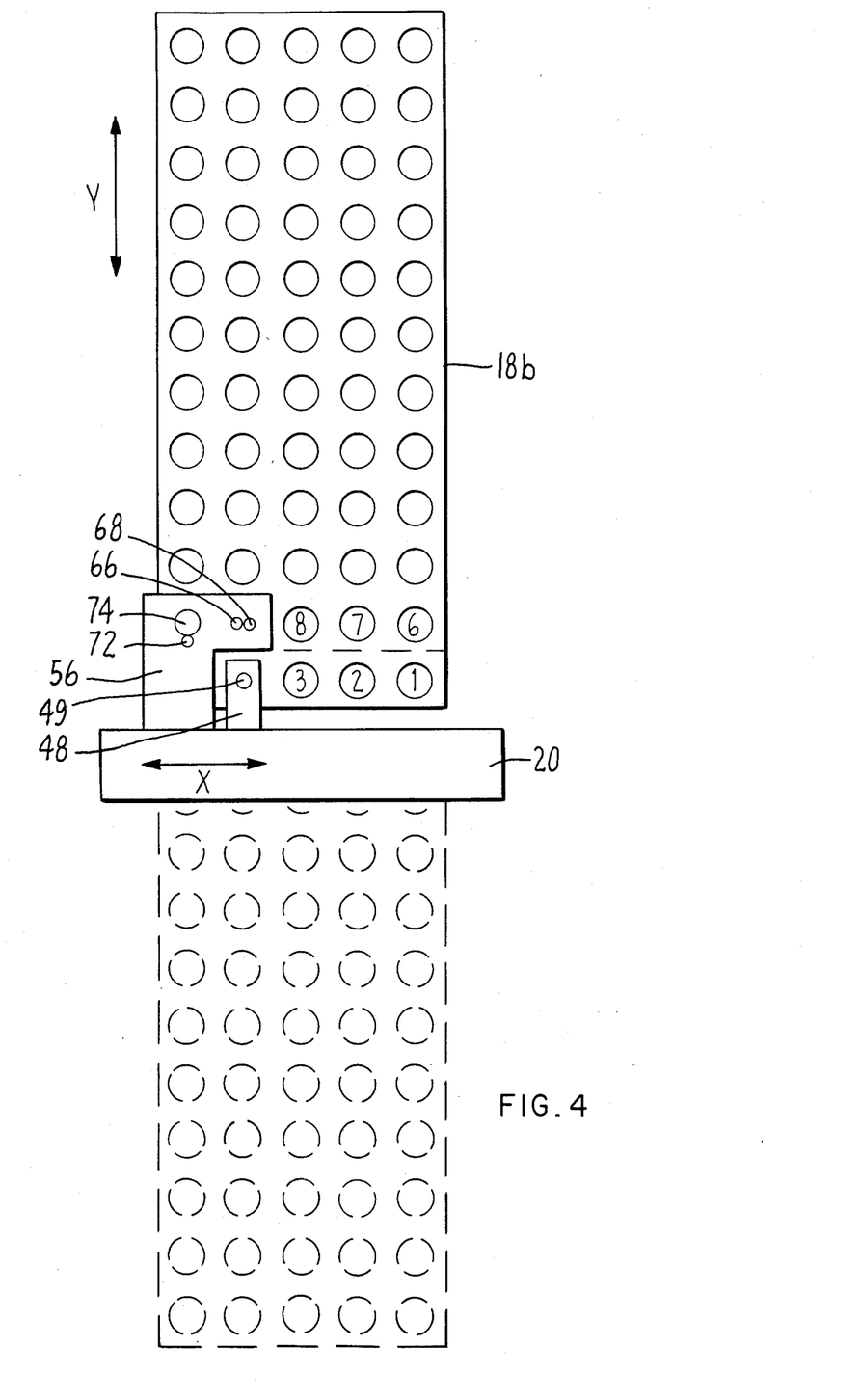
FIG. 4 is a top plan view of the reaction processor module.

Referring to the top plan view of FIG. 4, the relationship between the rack 18b, carriage 20 and the probe assemblies 48 and 56 is shown. Carriage 20 causes movement in the x-direction, along the rows of the rack 18b. Table 30, underneath rack 18b causes the rack 18b to be moved in the y-direction, along the columns of the rack. It will be recognized by those skilled in the art that the important aspect of this invention is the relative movement of the probes and the rack. While this embodiment is described with reference to a carriage having x-direction movement and a table accomplishing y-direction movement, two carriages can be used, or the table can effect x-direction movement. Each of these various configurations is intended to be within the scope of this invention and the claims appended hereto.

Referring now to FIG. 4, the wash cycle according to the present invention will be described. Row 1, consisting of five positions 1 through 5 and row 2, consisting of positions 6 through 11. This wash cycle commences after the antibody-antigen incubation period which occurs off the machine has ended and the rack 18b has been loaded into the reaction processor module. Once the automatic controller has confirmed the identity of the rack 18b and the type of assay to be performed, the wash cycle begins when the wash probes are inserted into the first tube in the first row (position 1).

For each individual tube, the first part of the wash cycle consists of aspirating the reagents and sample serum from the tube through probe 74, adding detergent through probe 72 and aspirating detergent through probe 74. These aspiration and addition steps are repeated again with the final step in the first half of the wash cycle being to add detergent to the tube through probe 72. This detergent addition corresponds to the "soak period" discussed above. The probe assembly 56 then extracts the wash probes 72 and 74 from the first tube. The rack table drive is then activated to position the wash probes over a preceding row of tubes to which detergent has already been added and which have been permitted to soak. Since the description relates to a first row of tubes, the description of the action on the preceding row is deferred until the second row. It must be recognized that the first row is a special case, different from the succeeding rows. After this sequence of registering with a tube position in the preceding row, but the same column, the wash probes register with the second position in the first row. The reagents and sample serum are aspirated, and then detergent is added and aspirated twice. Finally, the detergent probe 72 injects detergent fluid. According to the configuration of FIG. 4, the entire wash cycle has been completed in positions 1, 2, 3 and 4. The tube in position 5 will be completed after detergent has been dispensed into tube 10 and the table activated to register position 5 with the aspirating probe 74. Substrate has been added to positions 1, 2, 3 and 4 through substrate probe 66 which trails behind the wash probes 72 and 74 by one position in the same row.

Figure 5:
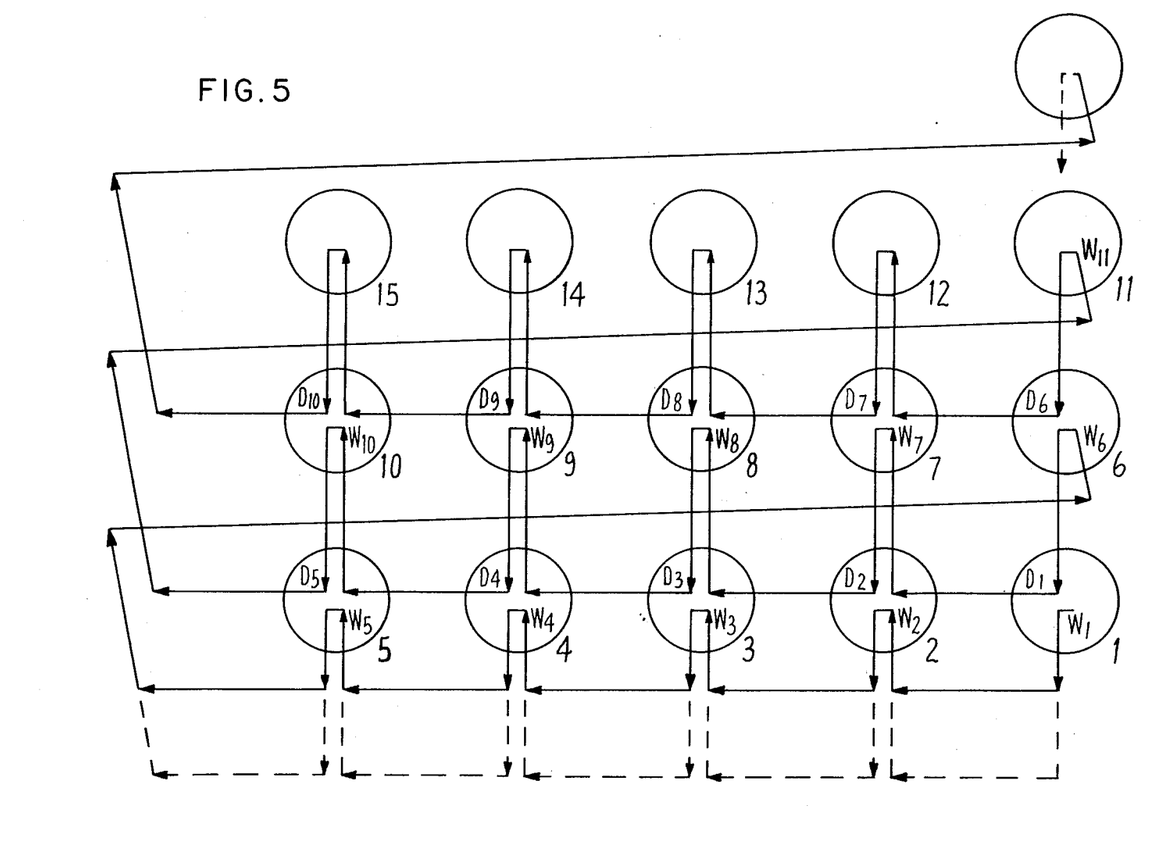
FIG. 5 is a schematic view of the relative movement of the detergent-dispensing and wash-aspirate probes of the present invention.

FIG. 5 shows the path of the probes and indicates when the specific steps of the cycle take place in a specific embodiment having at least 5 columns of tubes. Commencing with the tube in position 1, the above described series of detergent addition-aspiration steps occur, leaving tube 1 with a volume of detergent in which to soak ($W_1$) The wash probes 72 and 74 are then removed from the tube in the first position. Since the first row is a special case, in that there are no proceeding rows, the travel of the probes and the steps they perform are represented by dashed lines. $W_2$-$W_5$ are intended to represent completed first half wash cycles in each of the tubes in positions 2 through 5. It should be noted that the probe assembly and controller recognize a further position in the first row to the left of tube position 5. For completeness of describing the probes 72 and 74 travel, after the first half of the wash cycle has been performed upon position 5, the probes 72 and 74 move one further position so that the substrate 66/quench 68 probes also are inserted into each of the five positions across the row. In the first half of the wash cycle, no substrate is added to the tubes, but once the reaction tube has been "dried" according to the second half of the wash cycle, substrate is added to initiate the chromophore-forming reaction.

After detergent or wash fluid has been added to each of the tubes in positions 1 through 5, and the probes 72 and 74 have moved through the sixth position, the rack table is activated to move the rack one row's distance forward relative to the probes 72 and 74. Thus, the probes 72 and 74 are registered with a tube in the second row, in position 6, as indicated by the diagonal line and arrow. The probes 72 and 74 then go through the first half of the wash cycle in this position ($W_6$). After the probes 72 and 74 are removed from the tube in position 6, the rack table is again activated to move the rack one row's distance rearward relative to the probes 72 and 74. This time the movement of the rack is in the reverse, positioning probes 72 and 74 above the tube in position one. This tube one has been soaking in the detergent dispensed in the first pass through row one. However, in this second half of the wash cycle, the detergent previously dispensed is aspirated through probe 74 and one final aliquot of detergent is dispensed through probe 72. The final step in the wash cycle is to vacuum dry the tube in position one by aspirating through probe 74 ($D_1$, hereinafter D represents the second half of the wash cycle). Thereafter, the rack table is again activated to cause forward relative movement and the probes 72 and 74 are positioned over tube 7 for the first half of the wash cycle ($W_7$). When the rack again shifts to permit step ($D_2$) in position 2, the substrate probe 66, offset by one column from probes 72-174, is inserted into tube 1 and substrate reagent is added to the now dry tube one.

Thus, this invention permits multiple sequences to be performed in a single pass across the rack, yet permits incubation periods without extending the cycle time to a clinically impractical length.

Figure 6:
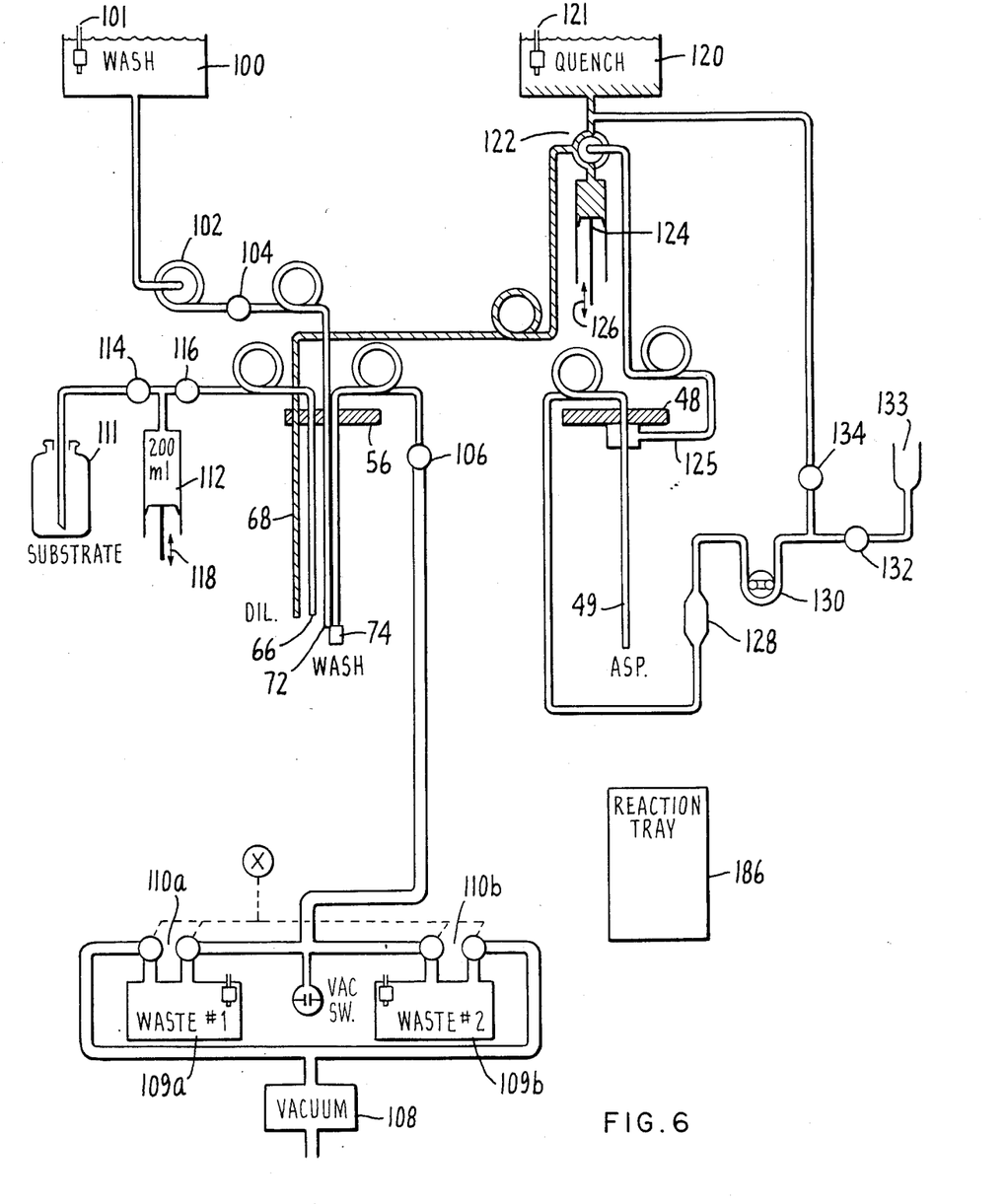
FIG. 6 is a process schematic showing the liquid storage and delivery system of the present invention.

FIG. 6 shows how the various fluids are delivered and aspirated on the reaction processing module. In the upper left of the figure, wash fluid is stored in a wash reservoir 100 whose liquid level is sensed by a wash liquid level sensor 101. Wash fluid flows from wash reservoir 100 to probe wash pump 102. A wash line solenoid-valve 104 is used to control flow in the wash fluid line. Wash fluid, also referred to in the specification as detergent, is dispensed from the detergent probe 72, depended from second probe assembly 56. In this embodiment, detergent is forcefully ejected from probe 72 to insure sufficient agitation and mixing to accomplish the wash steps. The wash aspirator probe 74, also depended from second probe assembly 56, is connected through a solenoid activated valve 106 to a vacuum pump 108 through waste reservoirs 190a and 109b. These reservoirs are used to store fluids aspirated from the various reaction tubes. Each reservoir has a control valve 110 which determines where the liquid will be stored.

Substrate reagent, used in chromophore formation, is stored in substrate reservoir 111. Since precise amounts (e.g., 200 ml.) of substrate must be dispensed, a substrate syringe 112 is used to withdraw fluid from the reservoir 111. Solenoid-activated valves 114 and 116 open and close to permit or to restrict flow of substrate reagent to and from the reservoir 111 and to and from the substrate probe 66. A substrate motor 118 is used to aspirate substrate from the reservoir 111 into the syringe 112 and to deliver substrate reagent from the syringe 112 to the probe 66 which is depended from the second probe assembly 56.

Quench reagent, which is added to the substrate reagent after a suitable enzyme substrate incubation period, is stored in quench reservoir 120. Liquid level in reservoir 120 is maintained by a level sensor 121. Quench reagent is used in the chromophore detection sequence and is also used to wash the aspirator probe 49 free of contaminants. In the detection sequence, precise amounts of quench reagent are required to insure reproducible results, particularly as compared to standards. Less precise delivery of quench reagent is required for the aspirator probe 49 wash. To accommodate both of these operating modes, the quench delivery system includes a three way valve and pump 122. This valve 122 communicates alternatively with the quench probe 68, a quench syringe 124 and a probe wash 125. In FIG. 6, this valve-pump 122 is positioned to communicate with the syringe 124 and probe 68. Syringe 124 is driven by a quench syringe motor 126.

The final component of the reaction processor module seen in FIG. 6 is the optics section. This part of the module is intended to quantitatively measure the signal generated in the reaction tubes. While the specification makes reference to a chromophore, implying spectrophotometric detection, it will be appreciated by those skilled in the art that other species of detectable signal are possible without varying from the scope of the present invention. For example, it is contemplated that fluorometric determinations could be made in the optics section. Referring to FIG. 6, an optics aspirator probe 49 is depended from the first probe assembly 48. Quenchedsubstrate is withdrawn from the subject reaction tube through a flow cell 128 by the action of a peristaltic pump 130. The spectrophotometric or fluorometric measurements are made on the fluid as it flows through the optics flow cell 128. Fluid leaving the peristaltic pump 130 passes through solenoid activated valve 132 and is briefly stored in an enlarged section 133. After measurement in the optics flow cell 128, the direction of the peristaltic pump 130 is reserved and the fluid is made to flow back into the reaction tubes through the aspirator probe 49. The inside of the aspirator probe 49, the flow cell 128 and perstaltic pump 130 are washed with quench reagent when valve 134 is open and valve 132 is closed. This prevents cross-contamination of sample results which leads to error in the technique.

Figures 7, 8:
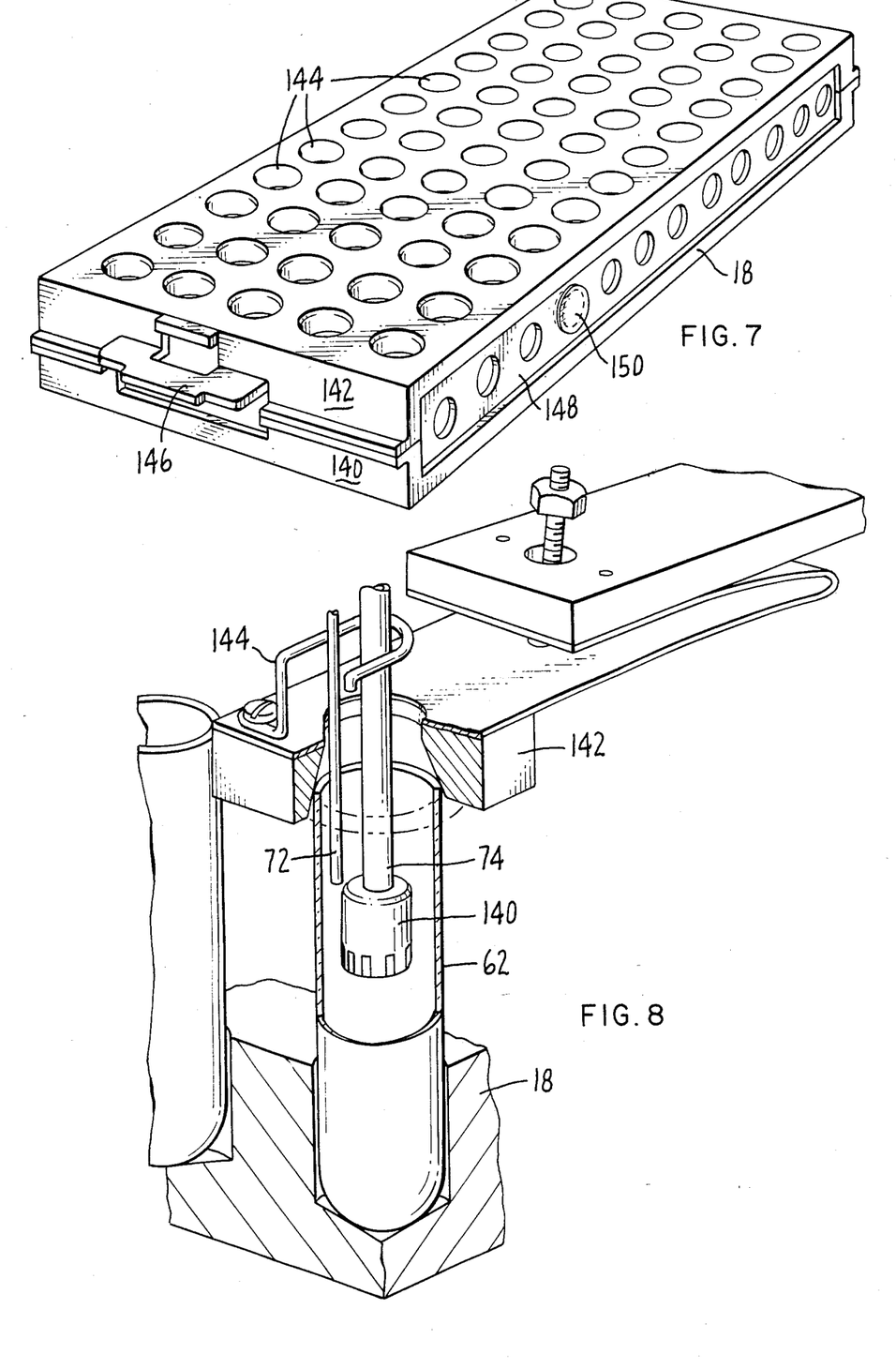
FIG. 7 is a perspective view of a reaction tube rack.
FIG. 8 is an exploded perspective view of the detergent-dispensing and wash-aspirate probes of the present invention, partially broken away.

The reaction tube rack of the present invention is shown in a perspective view in FIG. 7. The rack 18 is comprised of a lower half 140 and an upper half 142 which contains apertures 144 to receive the tubes. A handle 146 is provided at either end of the rack 18. One side panel 148 of the rack 18 also contains apertures 150 which are used to optically identify a rack of tubes. In this embodiment a reflective button is inserted in the aperture 150 and is optically detected by the instrument each time the rack 18 is loaded into the reaction processor module.

FIG. 8 shows the wash-aspirate 74 and detergentadding probe 72 in a reaction tube 62 which is held in place by the rack 18. The distal end 140 of the aspirate-probe 74 has an outside diameter which approaches that of the tube 62 mouth inside diameter. This large diameter permits intense aspiration, leaving a substantially dry bead at the end of the second half of the wash cycle. The wash probe 74 is connected to a shaft which moves vertically in conjunction with the probe assembly 58 (not shown in this figure). While the "basket" end 140 of the probe 74 is useful in drying the solid support bead at the end of the wash cycle, its large size makes accurate insertion of the probe essential. In order to stabilize the reaction tube mouth prior to insertion of the wash-aspirate probe 74, a tube trap 142 is provided to focus the tube mouth to coincide with the probe longitudinal axis. The tube trap 142 is lowered onto the tube mouth by cooperation with a bale 144 which is sized to mate with the outgoing basket 140. See our application Ser. No. 757,646. Other embodiments of the tube trap are described in our copending application Ser. No. 850,941, the relevant portions of which are incorporated herein by reference.

In summary, the present invention permits the introduction of an incubation period in an automated sequence wherein the incubation period is dependent upon a single tube position rather than upon an entire row, column or rack of tubes. This simple provision is made possible by arranging the probes to perform multiple sequences during a single pass of the probes through a rack of tubes. Thus, for example an eighty-five second wash-soak pause per tube is made possible without unduly extending the wash cycle time. The present invention introduces backtracking of the probes by a single row to permit completion of a wash cycle in one row while commencing the operation in the next row.

While the subject invention has been described with reference to a preferred embodiment, it will be appreciated by those skilled in the art that modifications and variations may be made which are within the scope of the invention and the claims appended hereto.

I claim:

1. A method for adding liquid to, and aspirating liquids from, reaction tubes disposed in rack comprising the steps of: providing reaction tubes disposed in a rack, said rack having n rows in a first horizontal x-direction and m columns in a second horizontal y-direction, perpendicular to the x-direction; a liquid probe depended from a carriage above said rack of tubes, said probe selectively moveable along its longitudinal axis relative to said carriage and perpendicular to the rack horizontal plane; means for moving said carriage in the x-direction or y-direction; means for selectively registering the liquid probe with a row of tubes in said rack; and, control means for selecting and effecting absolute and relative movement of the carriage, probe and rack;

introducing a controlled, timed, tube-dependent pause in a sequence for adding liquid to, and aspirating liquid from, a rack of reaction tubes by controlling the carriage and liquid probe movement so that     for each of $y=1$ to m columns,     a. liquid is added to tube in x row, y column;

b. previously-added liquid from tube in $(x-1)$ row, y column is aspirated;

c. carriage, rack and probe are returned to register said probe with the tube in x row, $(y+1)$ column; wherein x is between 1 and n.

2. The method of claim 1 wherein said liquid is detergent solution for use in immunoassays.

3. The method of claim 1 wherein said reaction tubes contain a solid support upon which is bound a member of an immunological pair.

4. An apparatus for adding liquid to, and aspirating liquids from, tubes which comprises:

a rack of reaction tubes, said rack having n rows in a first horizontal x-direction and m columns in a second horizontal y-direction, perpendicular to the x-direction, in a rectangular matrix, wherein $x=1$ to n rows, and $y=1$ to m columns;

means for receiving and positioning said rack;

a carriage above said rack;

at least one liquid probe depended from said carriage above said rack and selectively moveable along said probe longitudinal axis relative to said carriage;

means for selectively moving said carriage in the x-direction or y-direction;

means for selectively registering the liquid probe with a row of tubes in said rack;

control means for actuating said rack positioning means to move said rack discrete distances in the y-direction substantially equivalent to one column of tubes, relative to said probe, and for selecting movement of said carriage in the x-direction or y-direction; and,     second control means, for each of $x=1$ to n rows and $y=1$ to m columns, for first delivering liquid from said liquid probe to a tube located in x row, y column, for aspirating through the probe previously added liquid in a tube located at $(x-1)$ row, y column, and for returning said carriage, rack and probe to register said probe with the tube in x row, $(y+1)$ column.

5. The apparatus of claim 4 wherein said liquid probe has a relatively large outer diameter, as compared to the reaction tube inner diameter, to enable good aspiration and vacuum drying.

6. The apparatus of claim 4 further comprising a first and second liquid probe wherein the first liquid probe dispenses detergent solution and the second liquid probe aspirates detergent solution.

* * * * *